United States Patent
Nam et al.

(10) Patent No.: US 10,786,686 B2
(45) Date of Patent: Sep. 29, 2020

(54) METHOD FOR PREVENTING CANCERIZATION DUE TO LOW-DOSE IRRADIATION

(71) Applicant: KOREA HYDRO & NUCLEAR POWER CO., LTD., Gyeongsangbuk-do (KR)

(72) Inventors: Seonyoung Nam, Seoul (KR); Kwang Hee Yang, Seoul (KR); Su-Jae Lee, Seoul (KR); Rae-Kwon Kim, Gyeonggi-do (KR)

(73) Assignee: KOREA HYDRO & NUCLEAR POWER CO., LTD., Gyeongsangbuk-Do (KR)

( * ) Notice: Subject to any disclaimer, the term of this patent is extended or adjusted under 35 U.S.C. 154(b) by 0 days.

(21) Appl. No.: 16/096,563

(22) PCT Filed: Aug. 23, 2016

(86) PCT No.: PCT/KR2016/009300
§ 371 (c)(1),
(2) Date: Oct. 25, 2018

(87) PCT Pub. No.: WO2017/188516
PCT Pub. Date: Nov. 2, 2017

(65) Prior Publication Data
US 2019/0151679 A1    May 23, 2019

(30) Foreign Application Priority Data
Apr. 29, 2016    (KR) .................. 10-2016-0053592

(51) Int. Cl.
C12N 15/01    (2006.01)
A61N 5/10    (2006.01)
C12N 13/00    (2006.01)

(52) U.S. Cl.
CPC ........... *A61N 5/1031* (2013.01); *C12N 13/00* (2013.01); *C12N 15/01* (2013.01); *C12N 2529/00* (2013.01)

(58) Field of Classification Search
CPC ........... A61K 41/0019; A61K 41/0023; C12N 15/01; A61N 2005/0661; A61N 5/1038; A61N 5/1077; A61P 35/00
See application file for complete search history.

(56) References Cited

U.S. PATENT DOCUMENTS

| | | | | |
|---|---|---|---|---|
| 2003/0203361 | A1* | 10/2003 | Rosen ............... | C07K 14/4748 435/6.16 |
| 2011/0265197 | A1* | 10/2011 | Depinho ........... | A01K 67/0276 800/14 |
| 2015/0019190 | A1* | 1/2015 | Danter ................. | G16H 50/50 703/11 |

FOREIGN PATENT DOCUMENTS

| KR | 1020130086688 A | 8/2013 |
|---|---|---|
| KR | 1020150042590 A | 4/2015 |

OTHER PUBLICATIONS

Yin, E. et al., Gene Expression Changes in Mouse Brain After Exposure to Low-Dose Ionizing Radiation, Int. J. Radiat. Biol., Oct. 2003, pp. 759-775, vol. 79, No. 10.

(Continued)

*Primary Examiner* — David P Porta
*Assistant Examiner* — Fani Boosalis
(74) *Attorney, Agent, or Firm* — Standley Law Group LLP; Stephen L. Grant

(57) ABSTRACT

The present invention relates to a method for preventing cancerization of normal cells due to low-dose irradiation. The method enables effective prevention of cancerization of normal cells by means of low-dose radiation which is innocuous to a subject.

7 Claims, 16 Drawing Sheets

(56) References Cited

OTHER PUBLICATIONS

Chen, Y. et al., Mitochondrial Redox Signaling and Tumor Progression, Cancers, 2016, pp. 1-15 vol. 8, No. 40.
Suh, Y. et al., KRAS-driven ROS Promote Malignant Transformation, Molecular & Cellular Oncology, Jan. 22, 2015, vol. 2, Issue 2.
Kim, R. et al., Beneficial Effects of Low Dose Radiation in Response to the Oncogenic KRAS Induced Cellular Transformation, Scientific Reports, Oct. 30, 2015, pp. 1-10.
Kim, R. et al., Low Dose Radiation Promotes the Reduction of Malignant Phenotypes of the Transformed Breast Epithelial Cells, Korean Society of Radiation Bioscience, May 21, 2015.
United Nations Scientific Committee on the Effects of Atomic Radiation, Ionizing Radiation: Sources and Biological Effects, 1982 Report to the General Assembly.
Report of the United Nations Scientific Committee on the Effects of Atomic Radiation 2010.
Tubiana, M., Dose-Effect Relationship and Estimation of the Carcinogenic Effects of Low Doses of Ionizing Radiation: The Joint Report of the Academie Des Sciences (Paris) and of the Academie Nationale De Medecine, Int. J. Radiation Oncology Biol. Phys., 2005, pp. 317-319, vol. 63, No. 2.
Tubiana, M. et al., The Linear No-Threshold Relationship is Inconsistent with Radiation Biologic and Experimental Data, Radiology, Apr. 2009, pp. 13-22, vol. 251, No. 1.
AAPM Statement on Radiation Dose from Computed Tomography in response to the Brenner and Hall NEJM article published Nov. 29, 2007, Nov. 30, 2007, https://www.aapm.org/publicgeneral/CTScans.asp.
Brenner, D. et al., Computed Tomography—An Increasing Source of Radiation Exposure, The New England Journal of Medicine, Nov. 29, 2007, vol. 37, No. 22.

\* cited by examiner

METHOD FOR PREVENTING CANCERIZATION DUE TO LOW-DOSE IRRADIATION

TECHNICAL FIELD

The present invention relates to a method of preventing carcinogenesis of normal cells through low-dose irradiation.

BACKGROUND ART

In 1982, UNSCEAR (United Nations Scientific Committee on the Effects of Atomic Radiation. Ionizing radiation: sources and biologic effects. Vienna: United Nations; 1982.) reported that low-dose radiation is not associated with any mortality risk factors other than cancer. However, in a series of animal experiments, cancer-induced deaths did not account for all loss of life associated with radiation, which is more apparent based on data from recent years of a lifelong study on Japanese atomic bomb survivors. However, in a recent report published in 2010, cataracts are associated with low-dose radiation exposure, and there is a need to continue research into cardiovascular disease (United Nations Scientific Committee on the Effects of Atomic Radiation. Report of the United Nations Scientific Committee on the effects of atomic radiation. Vienna: United Nations; 2010.). In contrast, the French Academy of Sciences, led by Aurengo and Tubiana, claimed that there is a problem with extrapolating the exposure-influence relationship observed at high doses to low doses (Dose-effect relationship and estimation of the carcinogenic effects of low doses of ionizing radiation: the joint report of the Académie des Sciences (Paris) and of the Académie Nationale de Médecine. Int. J. Radiat. Oncol. Biol. Phys. 2005; 63:317-319. The linear no-threshold relationship is inconsistent with radiation biologic and experimental data. Radiology 2009; 251:13-22.). Also, the American Medical Physics Society (The AAPM statement on radiation dose from computed tomography, in response to the Brenner and Hall NEJM article published Nov. 29, 2007) refutes the opinion of Brenner and Hall (Brenner D. J., Hall E. J. Computed tomography: an increasing source of radiation exposure. N. Engl. J. Med. 2007; 357:2277-2284.) and suggests that standards for low-dose radiation are needed.

Radiation studies are limited to phenomena caused by high doses. For example, in a study of atomic bomb survivors, cancer incidence was significantly increased in survivors exposed to 100 mSv or more. However, it is very rare for normal people to be exposed to radiation of 100 mSv or more except in special cases, and estimating the relationship between radiation exposure and cancer in low-dose radiation exposure, as in CT imaging, is necessary for real-world populations. There should also be a survey of low-dose radiation exposure for workers in industries associated with radiation. In order to estimate cancer risk at 100 mSv or less, extrapolation using known data (cancer incidence from 100 mSv or more) is necessary, and many models are presented, but there are no clear guidelines.

Meanwhile, a gene that is likely to convert a normal gene into an oncogene due to various factors is called a proto-oncogene, Ras also being one of these genes. Ras protein formed by a Ras gene has a molecular weight of 21 kDa, and is specifically expressed in eukaryotic cells, and three types of Ras proteins (H-Ras, K-Ras, and NRas) are present in all animal cells. Ras protein is activated in response to external stimuli that activate a tyrosine kinase receptor. When the tyrosine kinase receptor is autophosphorylated by external stimuli, receptor activation is carried out in a manner in which an adaptor protein Grb2 for binding signal proteins forms a complex with SOS protein. The SOS protein is linked with the activated receptor to thus cause GDP/GTP exchange of inactive ras GDP that binds to the surrounding plasma membrane, whereby Ras is activated. The activated Ras plays a role in regulating cell proliferation and differentiation by activating various signal transduction pathways, such as the Raf-MAP kinase pathway.

It has been suggested that K-Ras in normal tissues regulates cell growth and differentiation, but K-Ras in cancer cells activates abnormal division and maintenance pathways and accumulates rapidly, resulting in malignancy and resistance to anticancer therapy, which ultimately cause recurrence of cancer. However, specific mechanisms for entities and interactions of tumor factors that regulate metastasis and maintenance of cancer cells have not yet been studied.

A number of papers and patent documents are referenced and cited throughout this specification. The disclosures of the cited papers and patent documents are incorporated herein by reference in their entirety to further clarify the level and scope of the subject matter to which the present invention pertains.

DISCLOSURE

Technical Problem

The present inventors have, through extensive research, developed a method of preventing carcinogenesis induced by a proto-oncogene, which has been suggested to be the main cause of cancer, and thus have ascertained that the carcinogenesis of normal cells may be prevented through low-dose irradiation, thereby culminating in the present invention.

Accordingly, an objective of the present invention is to provide a method of preventing the carcinogenesis of normal cells due to a proto-oncogene, comprising applying low-dose radiation to a mammalian subject.

The other objectives and advantages of the present invention will become more apparent from the following detailed description of the invention, claims and drawings.

Technical Solution

In order to accomplish the above objective, an aspect of the present invention provides a method of preventing the carcinogenesis of normal cells due to a proto-oncogene, comprising applying low-dose radiation to a mammalian subject.

Thorough research into the development of a method of preventing carcinogenesis due to a proto-oncogene, which is thought to be the main cause of cancer, carried out by the present inventors, resulted in the finding that carcinogenesis of normal cells may be prevented through low-dose irradiation.

As used herein, the term "radiation" refers to γ-radiation.

As used herein, the term "subject" refers to all organisms in which the process of carcinogenesis of cells due to an oncogene is capable of occurring in the body, and particularly indicates, for example, a mammal containing the Ras gene, by which cell carcinogenesis may progress. Especially, the term "subject" refers to a subject having high expression of a proto-oncogene or being suspected of carcinogenesis, i.e. a subject in which it is expected to be able to realize a preventive effect using the low-dose radiation of the present invention.

In an embodiment of the present invention, the mammalian subject of the present invention is a mammal other than a human. The oncogene, particularly the Ras gene, is also found in mammals other than humans, and low-dose radiation is applied to a mammal other than a human, thereby obtaining the same effect of inhibiting oncogene-induced malignant carcinogenesis as in the human.

As used herein, the term "low-dose radiation" refers to radiation of a relatively low cumulative dose compared to the cumulative dose of radiation that is conventionally used in the diagnosis and treatment of a patient. Typically, "low-dose radiation" is used as a generic term without particularly representing a cumulative dose.

In an embodiment of the present invention, low-dose radiation of the present invention has an absorbed dose of 1 Gy or less, particularly 0.01 Gy to 1 Gy, and more particularly 0.1 Gy to 1 Gy. The absorbed dose is an amount corresponding to the radiation-absorbed dose that is considered to be harmless to the mammalian subject. According to the method of the present invention, it is possible to suppress the carcinogenesis of normal cells by applying an absorbed dose of radiation that is harmless to a subject.

In an embodiment of the present invention, the proto-oncogene of the present invention is K-Ras. A gene that is likely to convert a normal gene into an oncogene due to various factors is called a proto-oncogene, Ras also being one of these genes. The Ras protein formed by the Ras gene has a molecular weight of 21 kDa, and is specifically expressed only in eukaryotic cells, and three types of Ras proteins (H-Ras, K-Ras, NRas) are present in all animal cells. The present invention provides a method of preventing the carcinogenesis of normal cells induced by K-Ras.

In an embodiment of the present invention, the carcinogenesis may be prevented by virtue of an increase in expression of GPx4 through the low-dose irradiation. GPx4 (Glutathione peroxidase 4) of the present invention is a protein belonging to the glutathione peroxidase protein family, and the present inventors have ascertained that the expression of GPx4 is increased through low-dose irradiation.

In an embodiment of the present invention, the increase in the expression of GPx4 causes the suppression of reactive oxygen species induced by K-Ras. The generation of reactive oxygen species by K-Ras has already been reported (Cell Death and Differentiation (2014) 21, 1185-1197). The reactive oxygen species are known to promote carcinogenesis of cells, and the present inventors have found that the malignant carcinogenesis inhibited in the present invention is associated with the regulation of reactive oxygen species.

Advantageous Effects

The features and advantages of the present invention are summarized as follows:

(a) The present invention provides a method of preventing carcinogenesis of normal cells induced by a proto-oncogene, comprising applying low-dose radiation to a mammalian subject.

(b) The method of preventing carcinogenesis according to the present invention is effective at preventing the carcinogenesis of normal cells using low-dose radiation harmless to a subject.

BEST MODE

Hereinafter, a detailed description will be given of the present invention.

A better understanding of the present invention will be given through the following examples, which are merely set forth to illustrate the present invention but are not to be construed as limiting the scope of the present invention, as will be apparent to those skilled in the art.

Example 1. Effect of Radiation on Normal Breast Cell Line

Figure 1A:
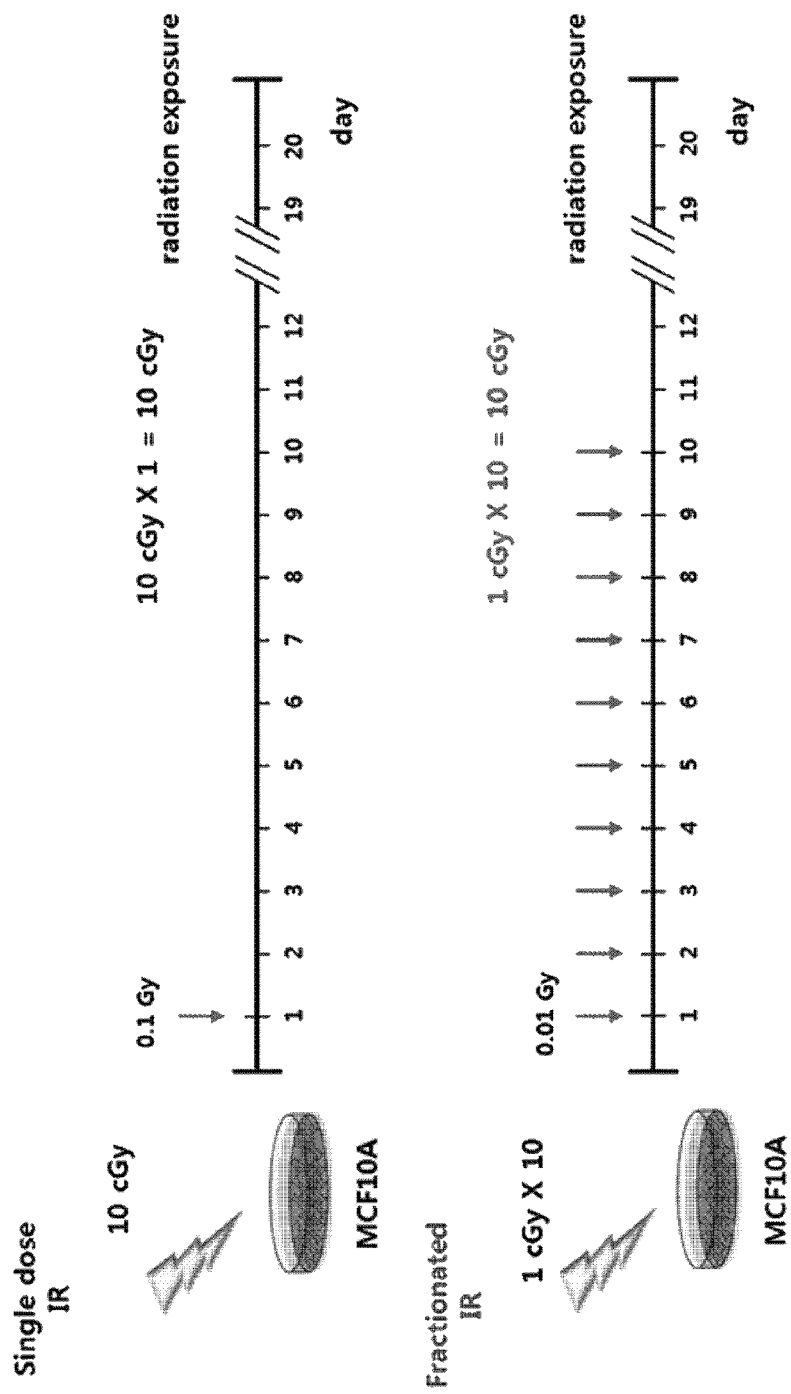
FIGS. 1A to 1C show the results of observing the effects of low-dose radiation on cell growth rate and cell death, FIG. 1A illustrating the single irradiation of 0.1 Gy and the fractionated irradiation of 0.01 Gy, FIG. 1B illustrating changes in cell number through low-dose irradiation on MSCV (Murine Stem Cell Virus) and low-dose irradiation on K-Ras over-expressed cells, and FIG. 1C illustrating the results of observing cell death using low-dose radiation.
Figure 1B:
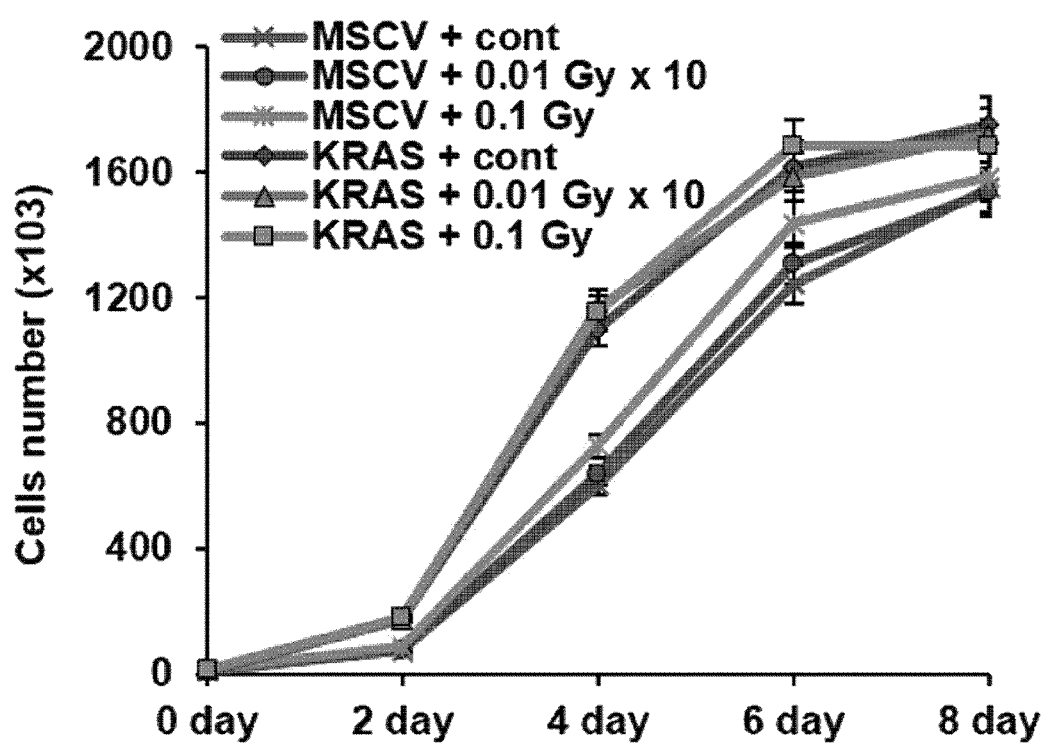
Figure 1C:
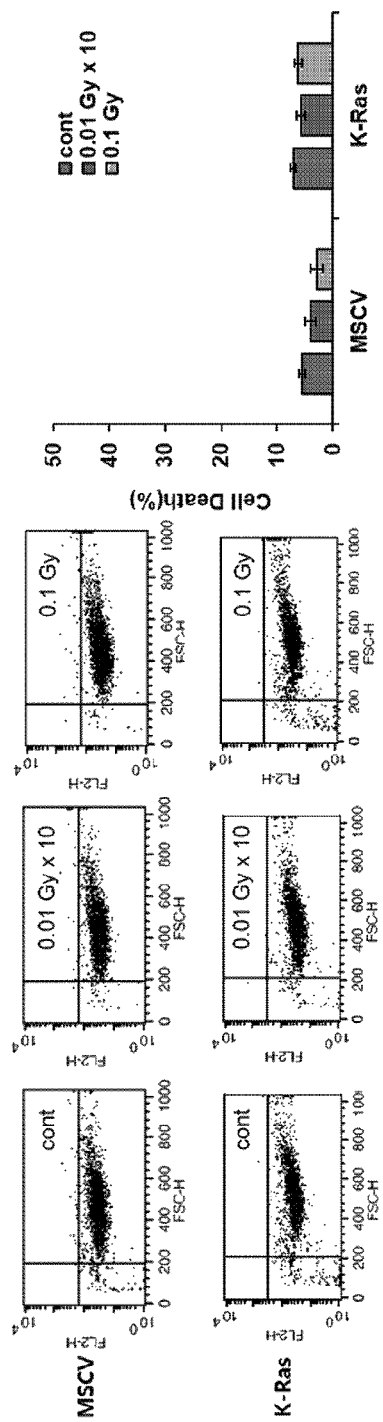

The normal breast cell line MCF10A was subjected to fractionated irradiation (10 times by 0.01 Gy each) and single irradiation (0.1 Gy alone) so as to reach a cumulative dose of 0.1 Gy (=10 cGy) (FIG. 1A), after which the cell growth rate and cell death were observed. Based on the results of comparison of cell growth rates through over-expression of the proto-oncogene K-Ras using an over-expression system through viral infection, the effects of low doses were not seen, but the growth rate was accelerated by K-Ras (FIG. 1B). In FIG. 1B, MSCV designates a control group, and KRAS+cont designates a test group for irradiation, in which the growth rate was increased. In order to evaluate whether cell death was caused by low-dose radiation, PI (Propidium iodide) staining was performed. As a result thereof, the cell death due to low-dose radiation and K-Ras was not observed (FIG. 1C). Thereby, it can be concluded that low-dose radiation has no influence on the cell growth rate or cell death and that K-Ras affects the cell growth rate.

Figure 2A:
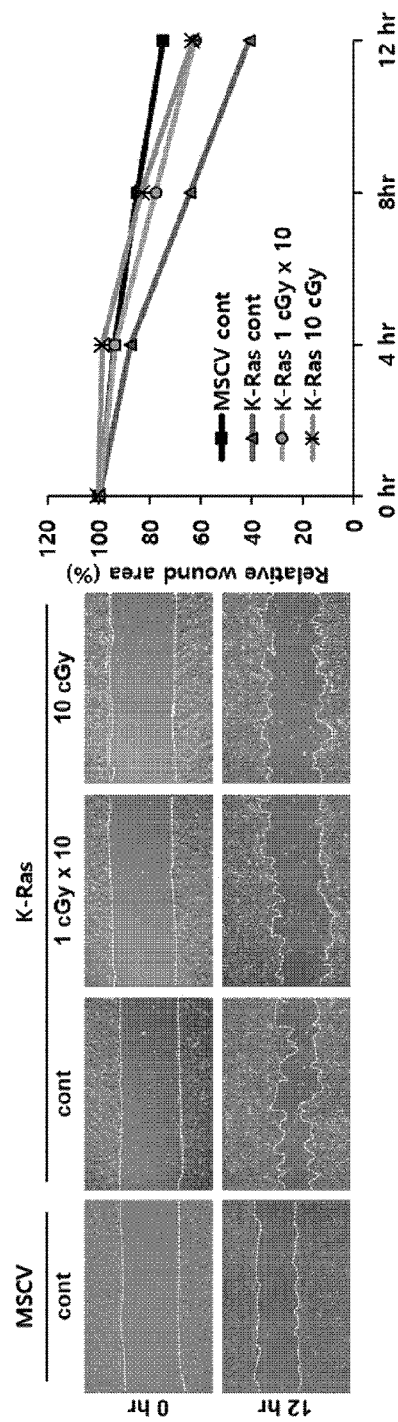
FIG. 2A to FIG. 2D show the results of observing cell migration, invasion and carcinogenesis upon over-expression of the proto-oncogene, FIG. 2A illustrating cell migration upon over-expression of the proto-oncogene, FIG. 2B illustrating cell invasion upon over-expression of the proto-oncogene, FIG. 2C illustrating the number of colonies produced upon over-expression of the proto-oncogene, and FIG. 2D illustrating the characteristic structural collapse of normal epithelial cells upon carcinogenesis of epithelial cells.
Figure 2B:
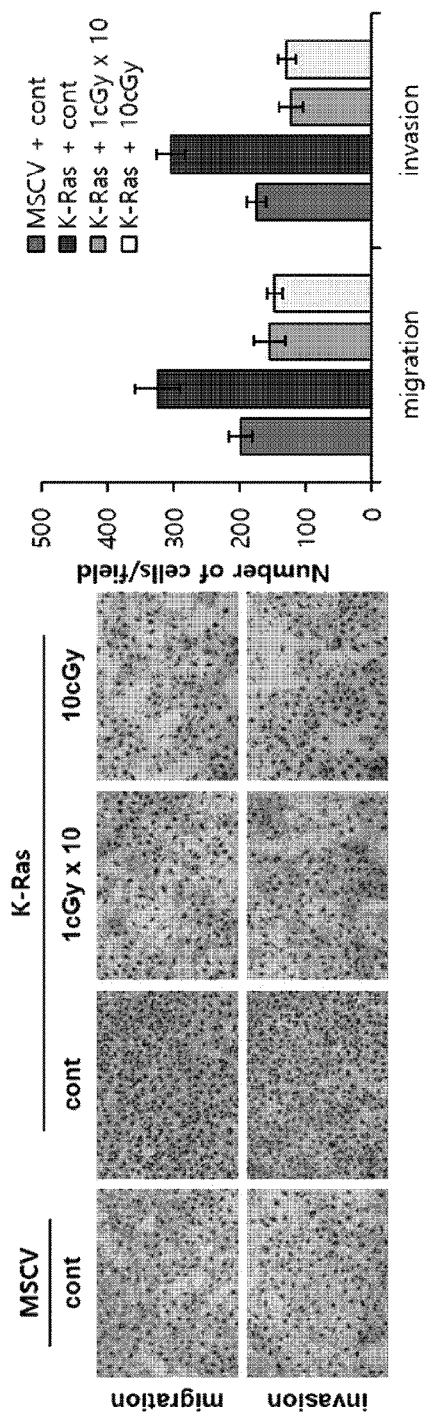
Figure 2C:
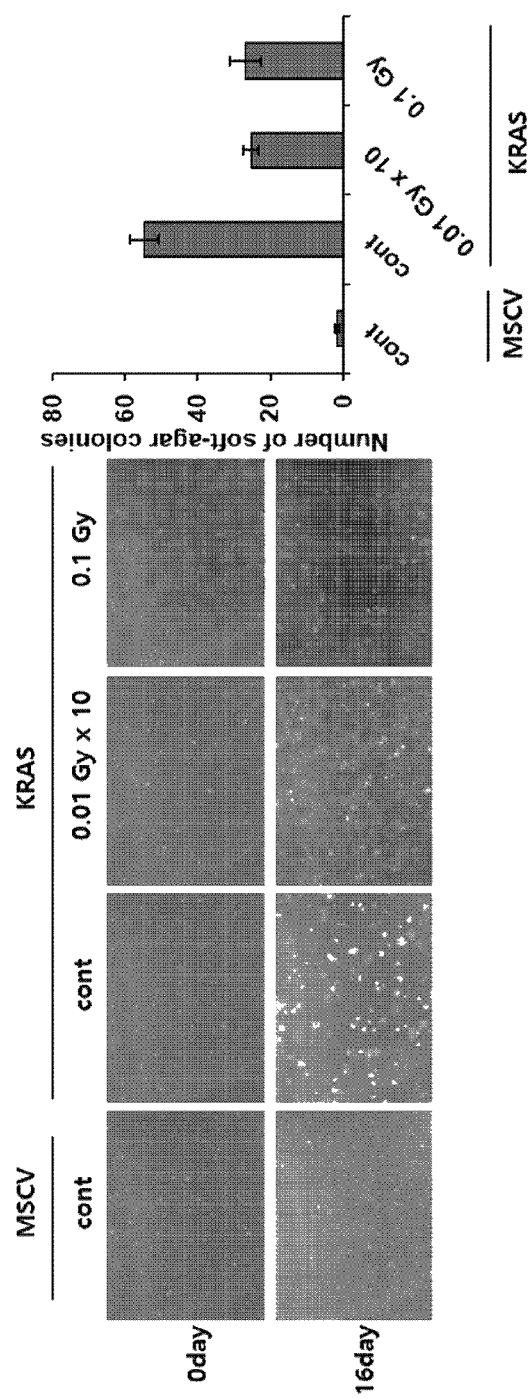
Figure 2D:
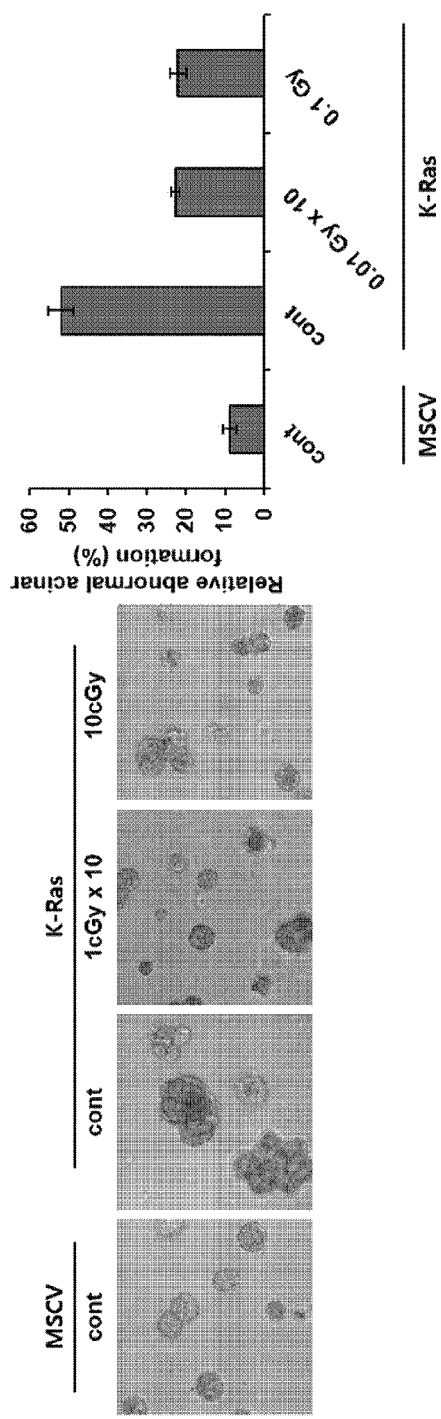

Example 2. Effect of Low-Dose Radiation on Carcinogenesis Induced by Proto-Oncogene In order to evaluate how low-dose radiation plays a role in the actions of the proto-oncogene, cell migration and invasion were analyzed using a trans-well. An increase in cell migration is a typical phenomenon of carcinogenesis. Accordingly, the migration of normal breast cells was measured through over-expression of the proto-oncogene (K-Ras). As a result thereof, the migration increased by the proto-oncogene was remarkably reduced in the group treated with low-dose radiation (FIG. 2A). In order to evaluate the cell invasion, in addition to the cell migration, the following test was performed. Specifically, the cells were seeded, after which predetermined thickness lines were drawn and changes in the intervals therebetween were observed over time, and thus the cell migration was measured. Like the above results, the cell migration and invasion increased by the proto-oncogene were reduced by low-dose radiation (FIG. 2B). In order to evaluate the carcinogenesis of cells, a soft agar assay was performed. Upon over-expression of the proto-oncogene, the colonies were formed, and the number thereof was significantly reduced in low-dose-irradiated cells (FIG. 2C). In the glandular epithelial cells, very well organized structures, especially polarized morphology, specialized cell-to-cell contact, attachment to an underlying basement membrane, etc. are observed. In particular, acinar spheroid forms with centrally localized hollow lumens are shown in 3D culture. The carcinogenesis of epithelial cells destroys such a characteristic structure to thereby induce abnormal acinar forms. The transformed cells were incubated using the extracellular matrix and thus the frequency of abnormal acinar spheroid forms was observed. Consequently, the cells having acinar forms showed abnormal forms by the proto-oncogene, and the number of abnormal forms was drastically decreased in the group treated with low-dose radiation (FIG. 2D). Thereby, the use of low-dose radiation can be concluded to inhibit carcinogenesis induced by the proto-oncogene.

Figure 3A:
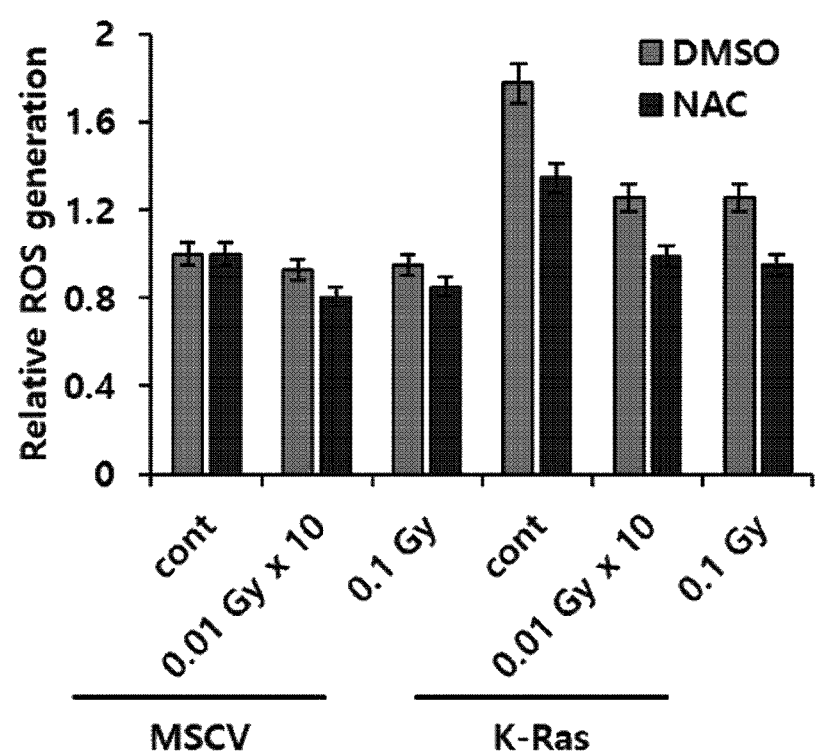
FIGS. 3A to 3D show the results of observing whether the inhibition of carcinogenesis through low-dose irradiation is based on the regulation of reactive oxygen species due to K-Ras, FIG. 3A illustrating the results of observing the reduction of reactive oxygen species through low-dose irradiation, FIG. 3B illustrating the results of observing the invasion induced by K-Ras upon treatment with N-acetylcysteine, which is known as an antioxidant, FIG. 3C illustrating the test results on the regulation of carcinogenesis by reactive oxygen species through soft agar assay, and FIG. 3D illustrating the results of observing acinar morphologies in a three-dimensional (3D) culture.
Figure 3B:
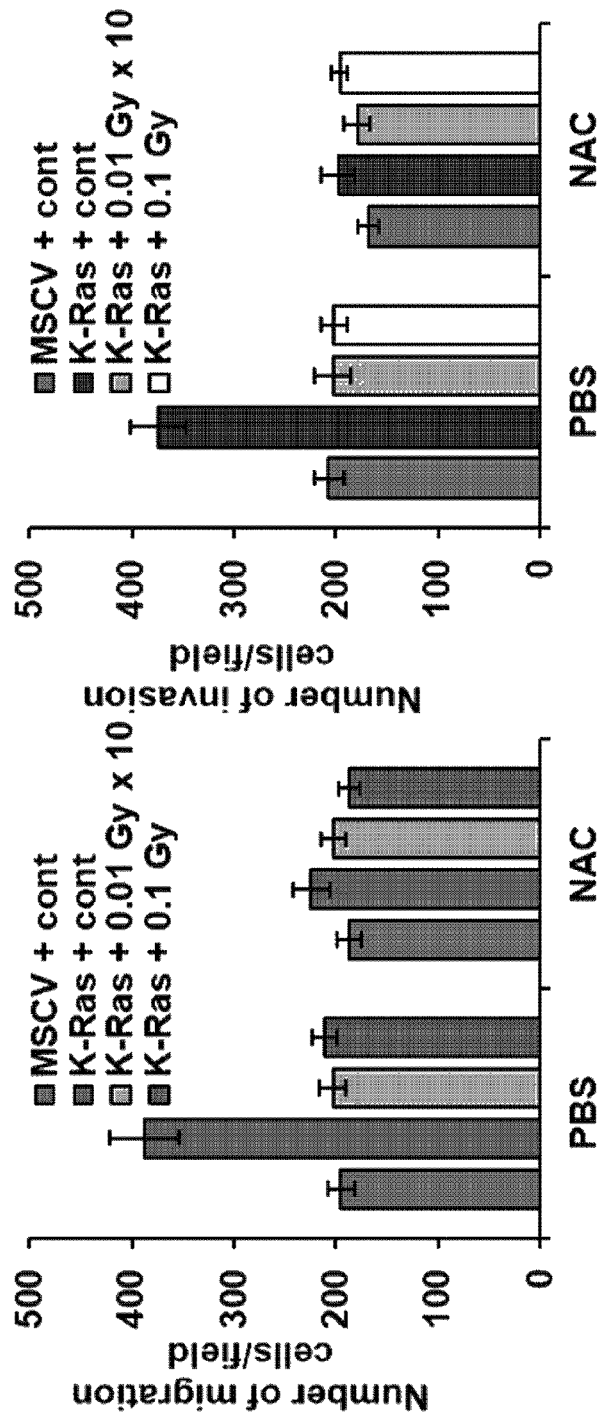
Figure 3C:
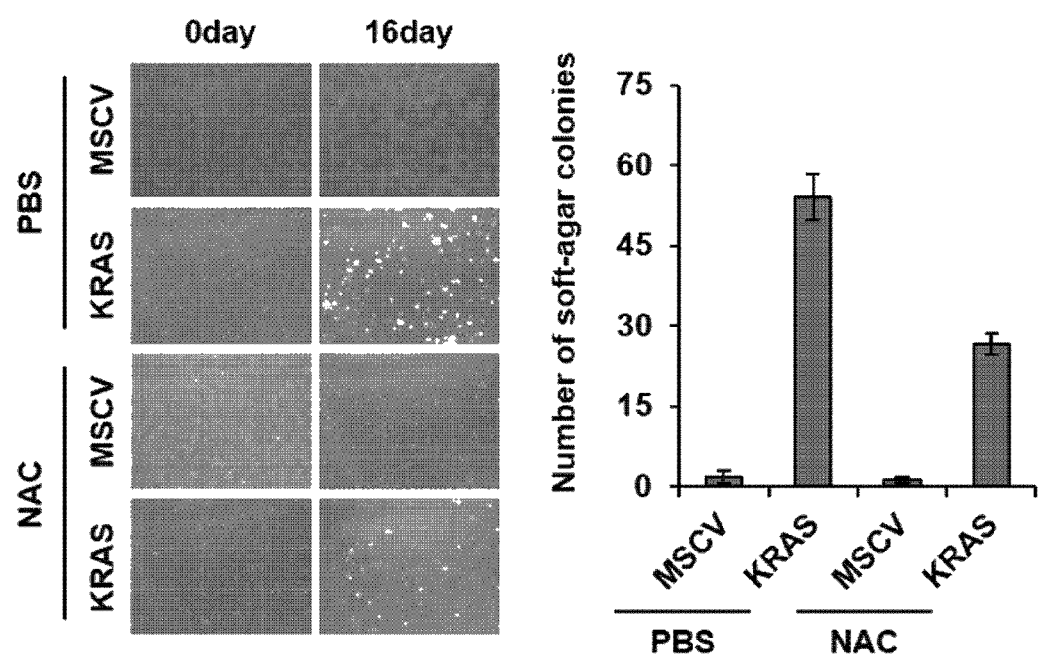
Figure 3D:
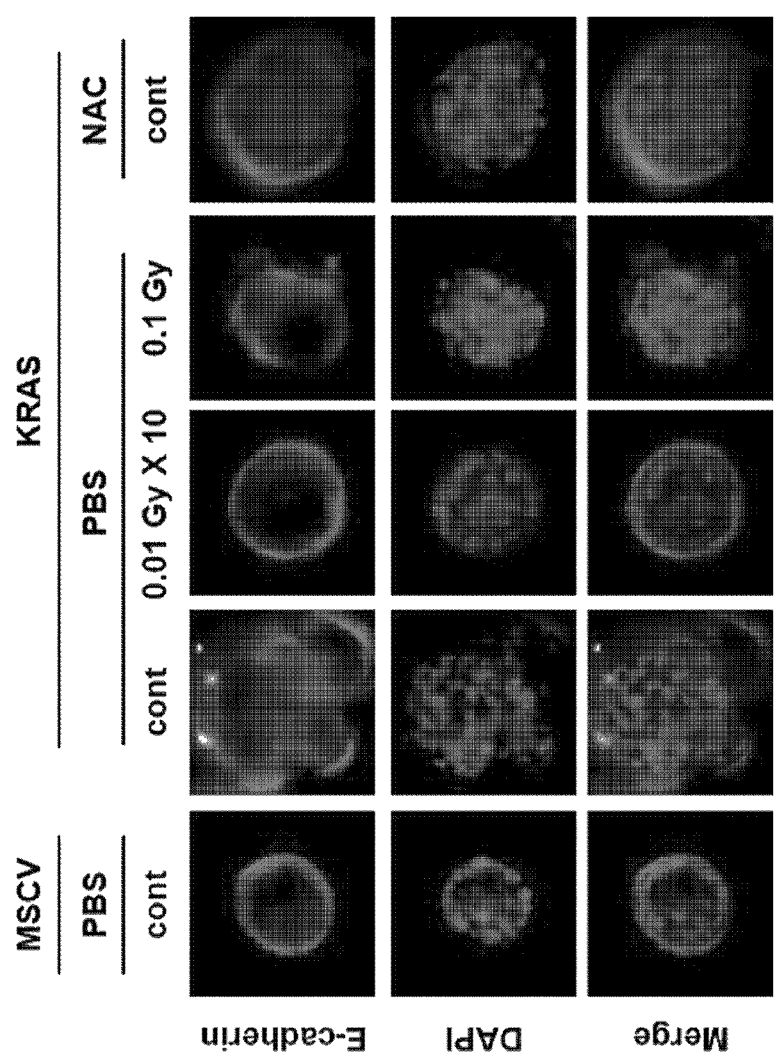

Example 3. Effect of Low-Dose Radiation on Generation of Reactive Oxygen Species The characteristics of breast epidermal cells were observed through 3D cell culture for the phenomenon of low-dose radiation itself, the phenomenon by the proto-oncogene, and the effect of low-dose radiation on the proto-oncogene phenomenon. The generation of reactive oxygen species (ROS) by K-Ras has already been reported. Since ROS is known to promote cell malignancy, it has been investigated whether cell malignancy inhibited by low-dose radiation is associated with the regulation of reactive oxygen species. The malignancy phenomena were observed through treatment with antioxidants for inhibiting reactive oxygen species, from which the effect of reactive oxygen species on malignancy was evaluated. Consequently, it was confirmed that the reactive oxygen species increased by the proto-oncogene were reduced by low-dose radiation (FIG. 3A). In order to evaluate whether malignancy was directly caused by reactive oxygen species, invasion induced by K-Ras was observed upon treatment with N-acetylcysteine (NAC), a known antioxidant. The cells were seeded in a predetermined amount into a Boyden chamber, and the number of cells that migrated to the opposite side of the chamber was observed. Consequently, cell invasion consistent with regulation in the concentration of reactive oxygen species was observed (FIG. 3B). In order to evaluate cell carcinogenesis, a soft agar assay was performed in a manner in which the cells were placed in agar and cell growth was observed in a 3D state. Upon treatment with the antioxidant, the number of colonies was reduced, from which regulation of carcinogenesis by reactive oxygen species was confirmed. Based on the results of observation of acinar forms in 3D culture, the same results as above were obtained (FIG. 3D). Thereby, the proto-oncogene K-Ras can be found to induce carcinogenesis through the regulation of reactive oxygen species.

Figure 4A:
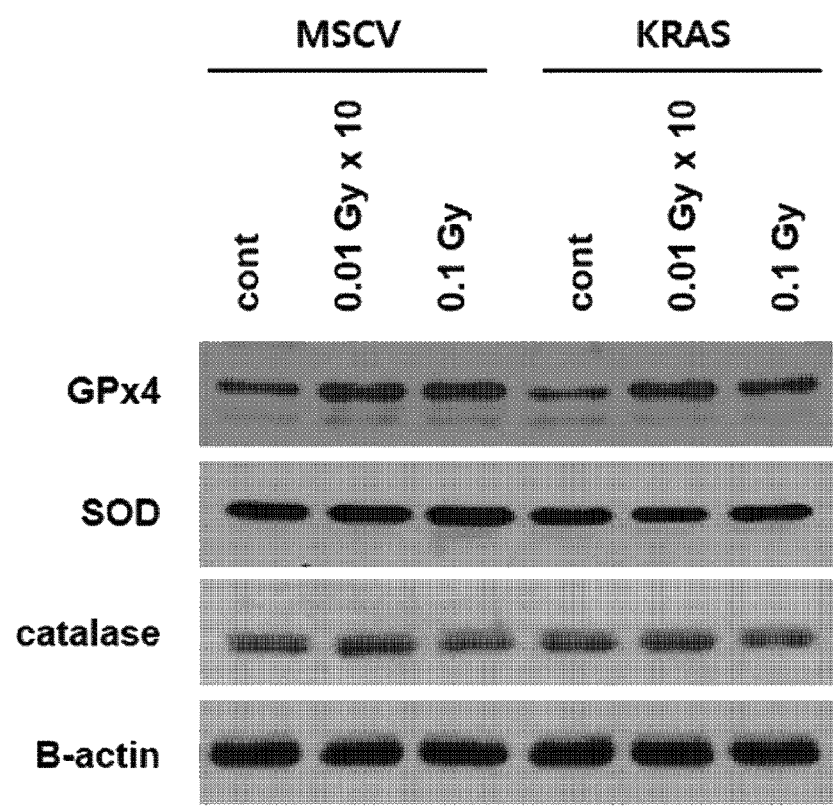
FIGS. 4A to 4E shows the results of evaluating how reactive oxygen species increased by the proto-oncogene are regulated in the low-dose-irradiated cells, FIG. 4A illustrating the increase in GPx4, among the antioxidant factors associated with reactive oxygen species, through low-dose irradiation, FIG. 4B illustrating the increase again in the concentration of reactive oxygen species when GPx4 is suppressed in the low-dose-irradiated cells, FIG. 4C illustrating the increase again in cell migration and invasion when GPx4 is reduced, FIG. 4D illustrating the same results through 3D culture, and FIG. 4E illustrating the same results through soft agar assay.
Figure 4B:
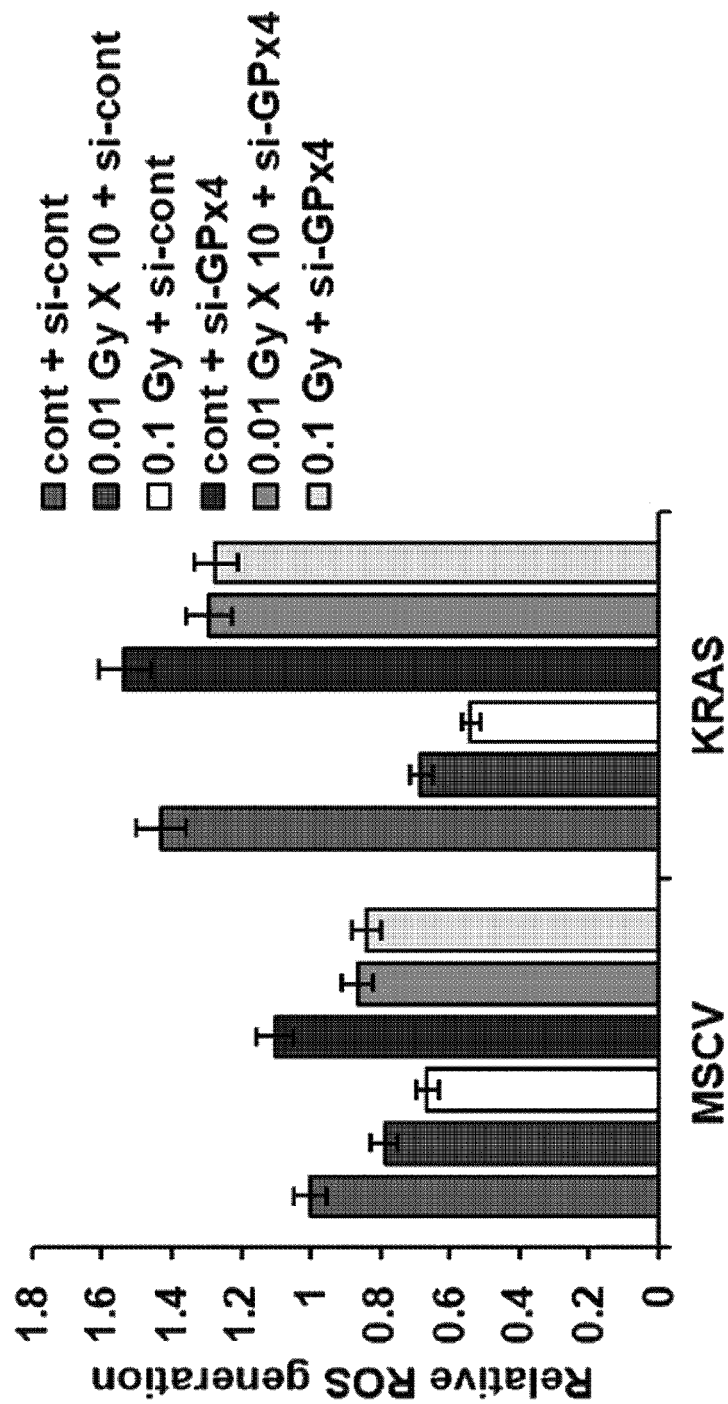
Figure 4C:
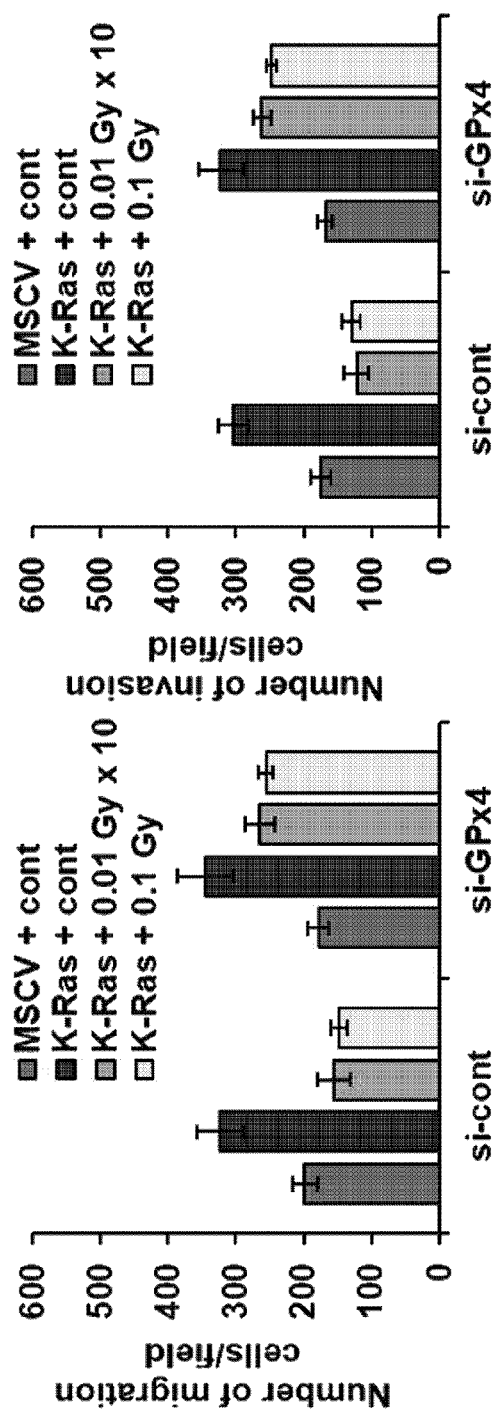
Figure 4D:
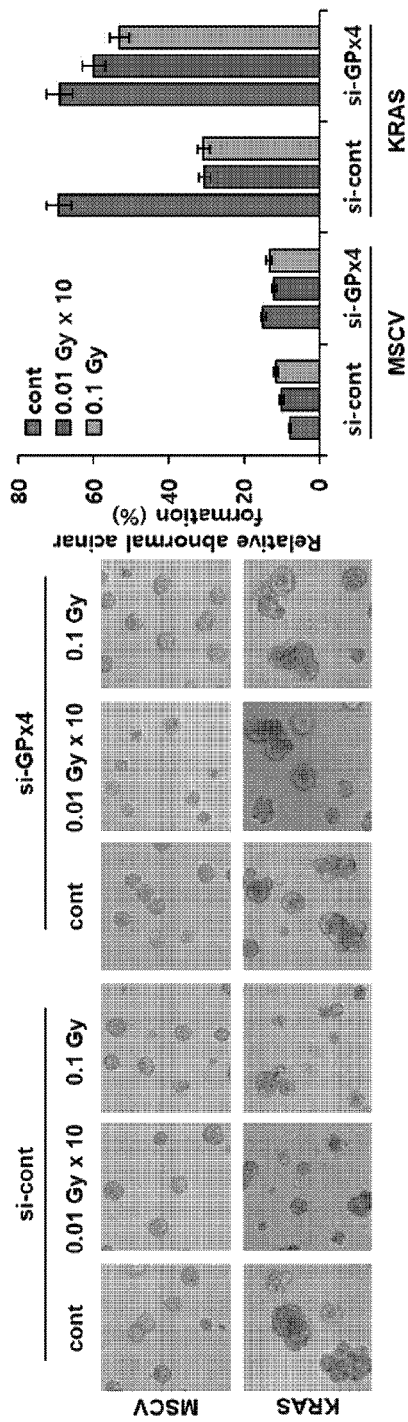
Figure 4E:
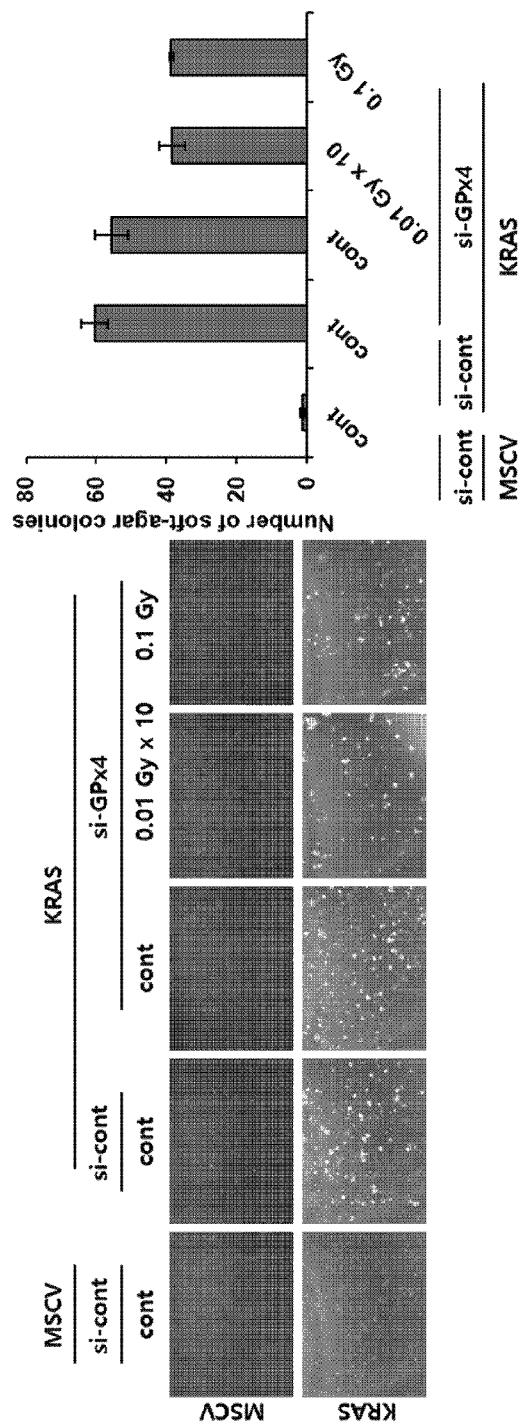

Example 4. Evaluation of Signal Transduction System Through Low-Dose Irradiation In order to evaluate the signal transduction system in cells through low-dose irradiation, expression of key proteins in the representative cell signal transduction system used by the proto-oncogene was confirmed by western blotting assay. How the reactive oxygen species increased by the proto-oncogene were regulated in the low-dose-irradiated cells was evaluated. Based on the results of measurement of antioxidant factors associated with ROS, the increase in GPx4 expression by low-dose radiation was observed through protein expression comparison using western blotting (FIG. 4A). When GPx4 was inhibited using siRNA in the low-dose-irradiated cells, the concentration of ROS, which was decreased in the low-dose-irradiated cells, was increased (FIG. 4B). Furthermore, when GPx4 was reduced, decreased cell migration and invasion were increased again (FIG. 4C). The results obtained through 3D culture were the same as the above test results (FIG. 4D), and the results of a soft agar assay were the same as above (FIG. 4E). In conclusion, the antioxidant factor GPx4 was increased in the low-dose-irradiated cells, whereby ROS induced by the proto-oncogene K-Ras was suppressed and thus carcinogenesis was inhibited.

Although the preferred embodiments of the present invention have been disclosed for illustrative purposes, those skilled in the art will appreciate that these embodiments are merely set forth to illustrate but are not to be construed to limit the scope of the present invention. Therefore, the substantial scope of the present invention will be defined by the appended claims and their equivalents.

What is claimed is:

1. A method of preventing carcinogenesis of a normal cell introduced by a proto-oncogene, said proto-oncogene comprising a K-Ras gene, said method comprising the step of applying low-dose radiation to a mammalian subject to increase expression of GPx4, thereby suppressing reactive oxygen species induced by K-Ras.

2. The method of claim 1, wherein the mammalian subject is a mammal other than a human.

3. The method of claim 1, wherein the low-dose radiation has an absorbed dose of 1 Gy or less.

4. A method of preventing carcinogenesis, introduced by a protooncogene, of a normal cell of a mammalian subject, comprising the step of applying a low-dose radiation to the subject, thereby increasing expression of GPx4.

5. The method of claim 4, wherein the mammalian subject is a mammal other than a human.

6. The method of claim 4, wherein the low-dose radiation has an absorbed dose of 1 Gy or less.

7. The method of claim 4, wherein the proto-oncogene is a K-Ras gene.

* * * * *